United States Patent [19]

Schoofs et al.

[11] Patent Number: 4,971,995
[45] Date of Patent: Nov. 20, 1990

[54] ALKYL OR BENZYL PHENOL ETHERS, THEIR PREPARATION AND THEIR THERAPEUTIC USES

[75] Inventors: Alain R. Schoofs, Paris; Michel Langlois, Buc; Christian R. Jeanpetit, Puteaux; Maryse F. Masson, Paris, all of France

[73] Assignee: Delande S.A., France

[21] Appl. No.: 301,706

[22] Filed: Jan. 26, 1989

[30] Foreign Application Priority Data

Feb. 5, 1988 [FR] France ................ 88 01373

[51] Int. Cl.$^5$ ............. C07C 255/50; C07C 43/225; A61K 31/275; A61K 31/085
[52] U.S. Cl. .......................... 514/520; 514/716; 514/718; 514/721; 549/333; 549/453; 558/51; 558/410; 558/423; 564/353; 568/442; 568/586; 568/644; 568/645; 568/648; 568/650; 568/662
[58] Field of Search ................ 568/644, 645, 586; 514/721, 520, 716, 718; 558/423

[56] References Cited

U.S. PATENT DOCUMENTS

| | | | |
|---|---|---|---|
| 3,987,108 | 10/1976 | Karrer | 568/644 X |
| 4,123,556 | 10/1978 | Karrer | 514/721 |
| 4,144,351 | 3/1979 | Grill et al. | 568/645 X |
| 4,152,461 | 5/1979 | Karrer | 514/721 |
| 4,471,116 | 9/1984 | Davidson et al. | 544/43 |

FOREIGN PATENT DOCUMENTS

| | | | |
|---|---|---|---|
| 2333526 | 1/1974 | United Kingdom | 568/644 |
| 2089345A | 6/1982 | United Kingdom | 568/644 |

OTHER PUBLICATIONS

J. Org. Chem. 1985, 50, 3125-3132.

Primary Examiner—Joseph Paul Brust
Attorney, Agent, or Firm—Roylance, Abrams, Berdo & Goodman

[57] ABSTRACT

Pharmaceutical or veterinary preparations containing (a) at least one compound with the formula:

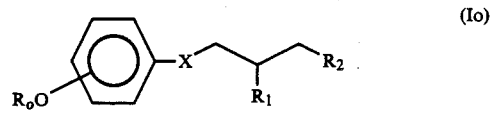

(Io)

where:

$R_o$ represents a $C_3$–$C_6$ alkyl group or a benzyl group with the formula:

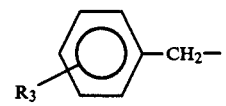

in which $R_3$=H, a halogen, a $C_1$–$C_4$ alkyl, a $C_1$–$C_4$ alkoxy, $CF_3$, $NO_2$ or a CN group; and $R_2$ represents:

a $C_1$–$C_4$ alkoxy group, in which case the pair (X, $R_1$)=(O, OH), (O, $C_1$–$C_4$ alkoxy), (CHOH, H), (O, H), (CH$_2$, H) or (CO, H);

and OH group, in which case the pair (X, $R_1$)=(O, OH), (O, $C_1$–$C_4$ alkoxy), (O, H) or (CH$_2$, H), with the reservation that when (X, $R_1$)=(O, OH), $R_o$ is different from a $C_3$–$C_6$ alkyl or a benzyl group; or a CN or $C_1$–$C_4$ alkyl-NH group, in which case the pair (X, $R_1$)=(O, H) or (CH$_2$, H), together with (b) a carrier or vehicle which is physiologically acceptable and appropriate for the compound used.

27 Claims, No Drawings

ALKYL OR BENZYL PHENOL ETHERS, THEIR PREPARATION AND THEIR THERAPEUTIC USES

The present invention relates to certain alkyl or benzyl phenol ethers which exhibit an inhibitive action on monoamine oxydases in general and type B monoamine oxydase in particular.

The formula of these ethers can be written more precisely as:

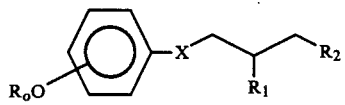

(Io)

where:

$R_o$ represents a $C_3$–$C_6$ alkyl group or a benzyl group with the formula:

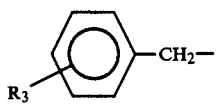

in which $R_3$=H, a halogen, a $C_1$–$C_4$ alkyl, a $C_1$–$C_4$ alkoxy, $CF_3$, $NO_2$ or a CN group; and $R_2$ represents:
a $C_1$–$C_4$ alkoxy group, in which case the pair $(X, R_1)$=(O, CH), (O, $C_1$–$C_4$ alkoxy), (CHOH, H), (O, H), ($CH_2$, H) or (CO, H);

an OH group, in which case the pair $(X, R_1)$=(O, OH), (O, $C_1$–$C_4$ alkoxy), (O, H) or ($CH_2$, H), with the reservation that when $(X, R_1)$=(O, OH), $R_o$ is different from a $C_3$–$C_6$ alkyl or a benzyl group; or a CN or $C_1$–$C_4$ alkyl-NH group, in which case the pair $(X, R_1)$=(O, H) or ($CH_2$, H).

With the exception of the compound for which the set $(R_2, X, R_1)$ denotes (OH, O, H) and $R_oO$ represents the group

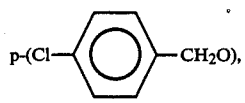

these ethers are new and these new ethers correspond to the formula:

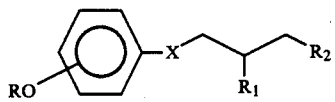

(I)

where:

R represents a $C_3$–$C_6$ alkyl group or a benzyl group with the formula:

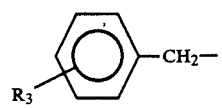

in which $R_3$=H, a halogen, a $C_1$–$C_4$ alkyl, a $C_1$–$C_4$ alkoxy, $CF_3$, $NO_2$ or a CN group; and $R_2$ represents:
a $C_1$–$C_4$ alkoxy group, in which case the pair $(X, R_1)$=(O, OH), (O, $C_1$–$C_4$ alkoxy), (CHOH, H), (O, H), ($CH_2$, H) or (CO, H);

an OH group, in which case the pair $(X, R_1)$=(O, OH), (O, $C_1$–$C_4$ alkoxy), (O, H) or ($CH_2$, H), with the reservations that:
* when $(X, R_1)$=(O, OH), R is different from a $C_3$–$C_6$ alkyl or a benzyl group; and
* when $(X, R_1)$=(O, H), RO is different from

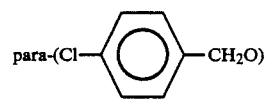

and ortho-benzyloxy;

a CN group, in which case the pair $(X, R_1)$=(O, H) or ($CH_2$, H); or a $C_1$–$C_4$ alkyl-NH group, in which case the pair $(X, R_1)$=(O, H) or ($CH_2$, H) with the reservation that when $(X, R_1)$=(O, H) and $R_2$=NH—$CH_3$ or

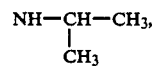

RO is different from para-benzyloxy.

Thus, the primary object of the present invention relates to these newly discovered ethers (I).

Within the range of ethers (Io) and (I), the preferred compounds are those for which RO is situated in the para position, whilst within this sub-range the preferred compounds are those for which $R_3$ is situated in the meta position.

Moreover, when $R_1$ and $R_2$ represent a $C_1$–$C_4$ alkoxy group, the methoxy group is preferred.

Furthermore, when $R_1$ differs from a hydrogen atom, the compounds in question are antimeric, and consequently exist in the form of two enantiomers; accordingly, the present invention covers each of these enantiomers and their mixtures including the racemic mixtures.

In the above description and following text, the term "$C_3$–$C_6$ alkyl group" denotes a linear or branched hydrocarbon chain having from 3 to 6 carbon atoms, and more particularly including n-propyl, iso-propyl, n-butyl, sec-butyl, iso-butyl, tert-butyl, amyl and hexyl groups; the term "halogen" denotes fluorine chlorine, bromine or iodine; the term "$C_1$–$C_4$ alkyl" denotes a branched or linear hydrocarbon chain having up to 4 carbon atoms, and more particularly including methyl, ethyl, n-propyl, iso-propyl, n-butyl, sec-butyl, iso-butyl and tert-butyl groups; and the term "$C_1$–$C_4$ alkoxy group" has the formula —O—($C_1$–$C_4$ alkyl).

The present invention further relates to processes for the preparation of the compounds (I), in conformity with the reaction schemes 1 to 10 described below.

Reaction scheme 1

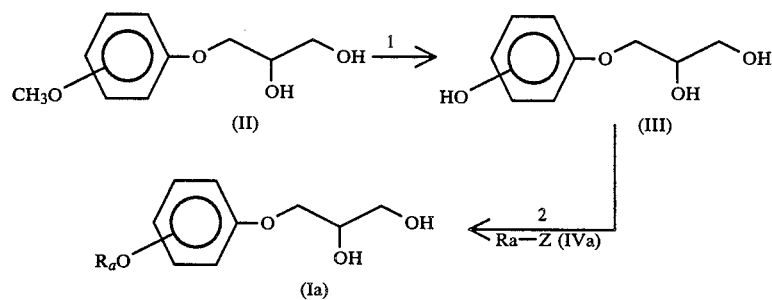
Reaction scheme 2
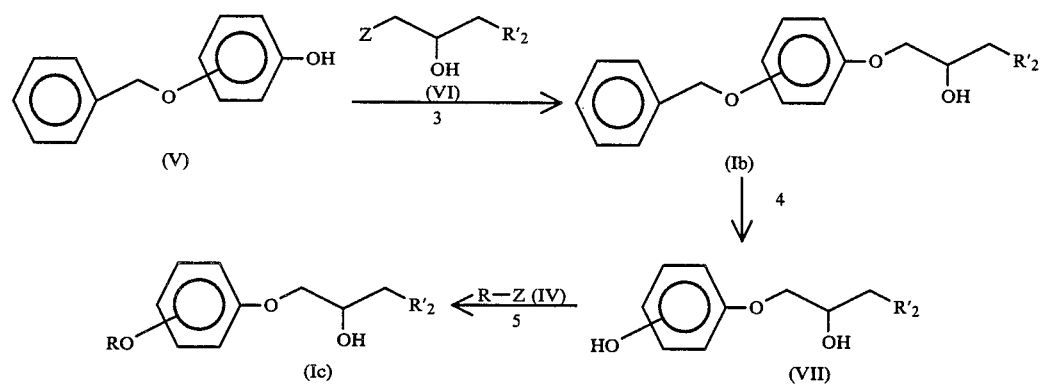
Reaction scheme 3
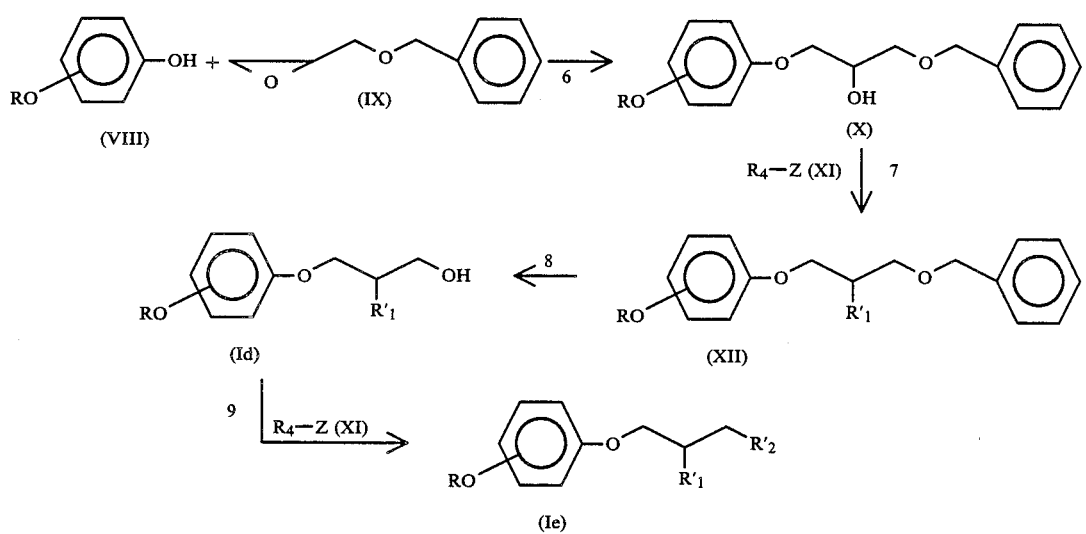
Reaction scheme 4
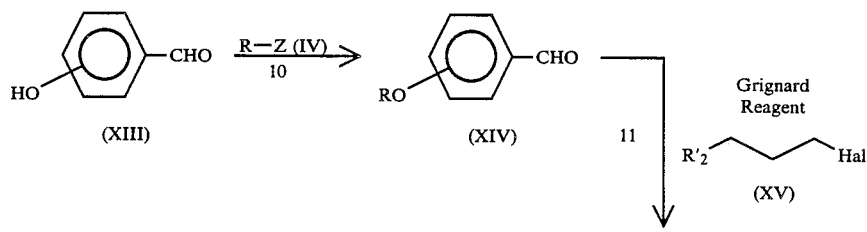

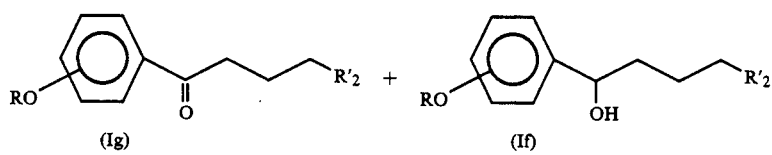
Reaction scheme 5
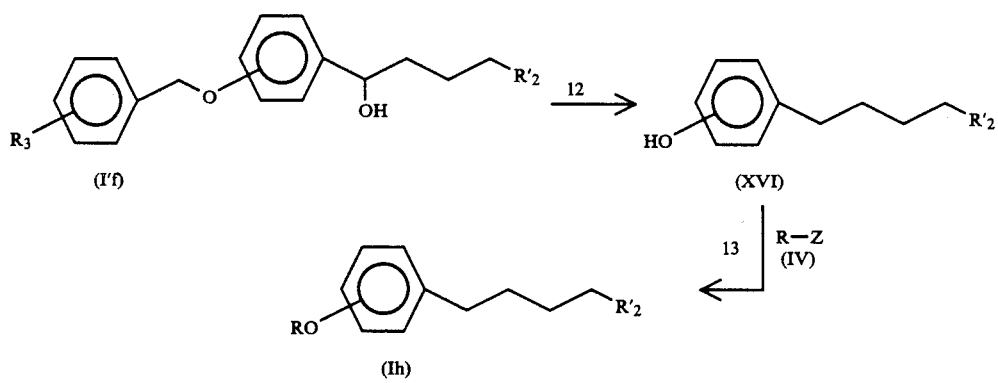
Reaction scheme 6
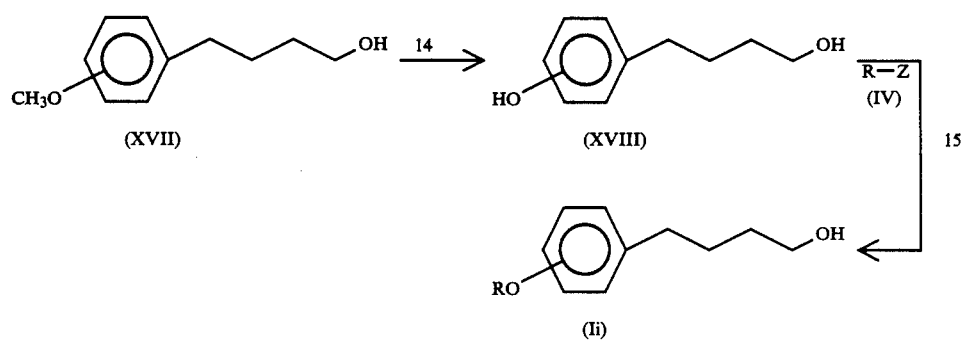
Reaction scheme 7
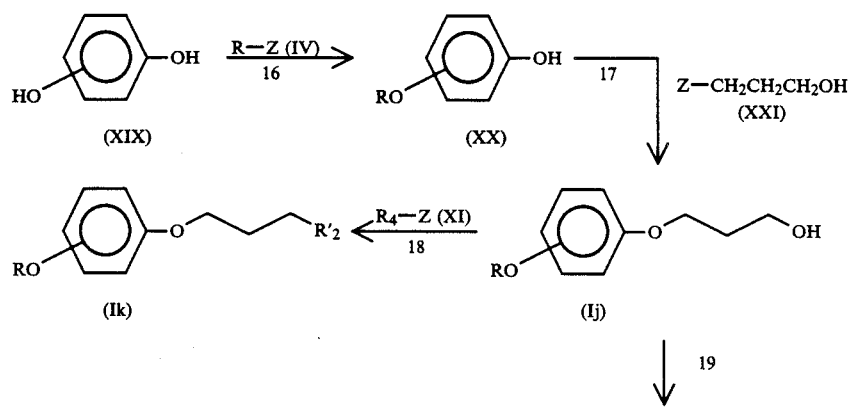

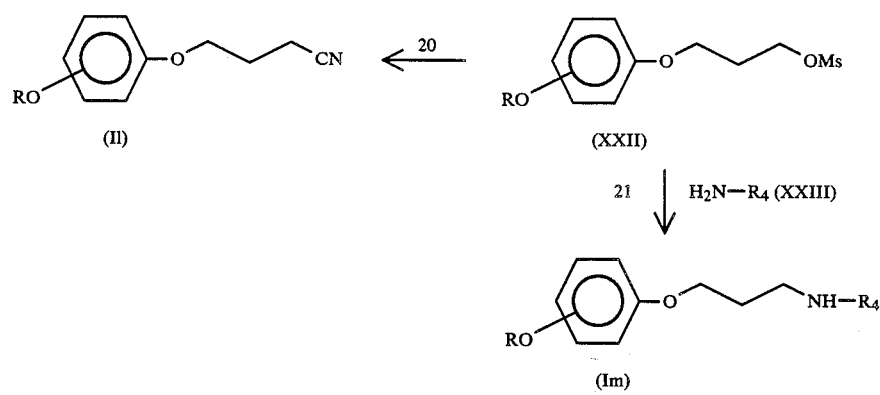
Reaction scheme 8
Reaction scheme 9 (stereospecific synthesis)
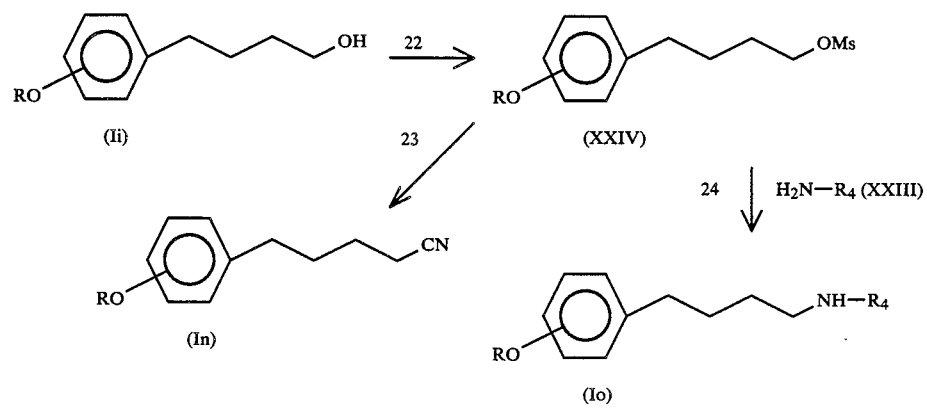
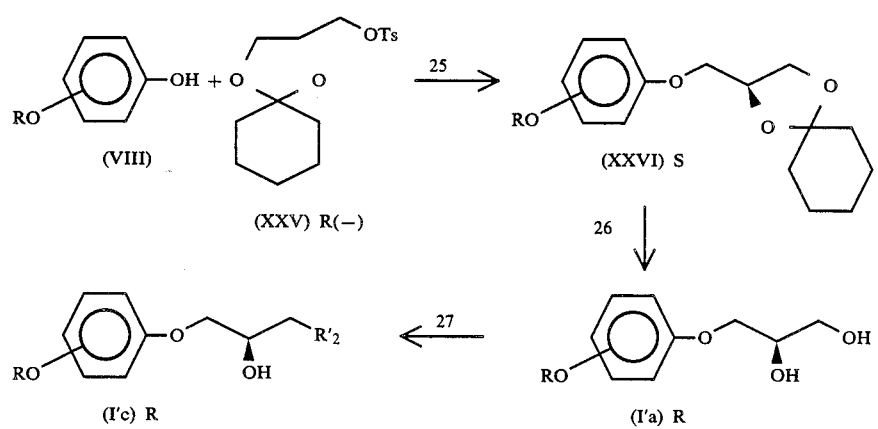

Reaction scheme 10 (stereospecific synthesis)

The various symbols appearing in the above reaction schemes have the following significations:

R: as in formula (I),
Ra: the same as R in formula (I), excepting $C_3$–$C_6$ alkyl and benzyl groups.
Z: a readily substitutable group such as a halogen atom,
$R_2'$: a $C_1$–$C_4$ alkoxy group,
$R_4$: a $C_1$–$C_4$ alkyl group,
$R_1'$: a $C_1$–$C_4$ alkoxy group,
$R_3$: as in formula (I),
Ms: mesyl group,
Ts: tosyl group.

| | | | | |
|---|---|---|---|---|
| 1 | 14 | | | hot demethylation in 48% HBr, |
| 2 | 5 | 10 | 13 15 | |
| 16 | 17 | 25 | 28 | O-alkylation, preferably in the presence of a base such as $K_2CO_3$, |
| 3 | | | | condensation brought about in the presence of a base such as KOH and a phase transfer catalyst, in a two-phase medium, |
| 4 | 8 | | | debenzylation by hydrogenolysis in the presence of palladium on carbon, |
| 6 | | | | condensation in the presence of a base such as $K_2CO_3$, |
| 7 | 9 | 18 | | O-alkylation in the presence of a metal hydride such as sodium hydride, |
| 12 | | | | hydrogenation in a hydrochloric medium in the presence of palladium on carbon, |
| 19 | 22 | | | reaction with mesyl chloride, |
| 20 | 23 | | | reaction with an alkali metal cyanide, |
| 26 | 29 | | | acid hydrolysis, |
| 27 | 30 | | | reaction with tosyl chloride followed by reacting the resulting tosylate with an alkali metal alcoholate corresponding to the alcohol $R'_2H$, |
| 11 | | | | reaction with a Grignard reagent, |
| 21 | 24 | | | N-alkylation. |

It should be noted that the tosylates (XXV) and (XXVII) can be prepared by the wellknown classical procedures familiar in the art, starting with the corresponding alcohols, or synthesized by published procedures.

More particularly, the alcohol with the formula:

can be synthesized by means of the procedure described by T. SUGYAMA, H. SUGAWARA, M. WATA-NABE and K. YAMASHITA (Agric. Biol. Chem., 1984, 48, 1841-1844), while the alcohol with the formula:

can be synthesized by means of the procedures described in

E. BAER and H. O. L. FISHER (J. Amer. Chem. Soc., 1939, 61, 761–765),

C. M. LOK, J. P. WARD and D. A. VANDORP (Chem. Phys. Lipids, 1976, 16, 115–122), and M. E. JUNG and T. S. SHAW (J. Amer. Chem. Soc., 1980, 102, 6304–6311).

Furthermore, the enantiomers of compounds (Id) and and (Ie) can be synthesized in a stereospecific manner by the reaction scheme 3 set out above, in which the compound (IX) is either the enantiomer or the enantiomer both of which enantiomers can be prepared by the procedure described by S. TAKANO, M. AKIYAMA and K. OGASAWARA (Synthesis, 1985, 503–504).

Finally, the enantiomers of the alcohols (If) can be prepared by the classical separation procedures described by J. JACQUES, A. COLLET and S. H. WILEN ("Enantiomers, Racemates and Resolutions", Wiley-Intersciences, 1981, pp. 332–354).

The following preparations are intended to illustrate the invention by describing procedures by way of example.

Example 1: (hydroxy-4 phenoxy)-3 propanediol-1,2 (±)

((III); code number 340481)

After introducing 140 ml of 48% HBr, drop by drop, to a vessel containing 30 g (0.151 mole) of (methoxy-4 phenoxy)-3 propanediol-1,2 (±), the vessel is shaken for 48 hours at 50° C. After gradual salification with 100 ml of NH$_4$OH 10N and extraction with CH$_2$Cl$_2$ (pH ca. 1–2), the aqueous phase is evaporated substantially to dryness and taken up in hot ethyl acetate. The impure product recrystallized in ethyl acetate yields 20.5 g of a crystalline solid corresponding to the expected pure product (MP 132° C.).

TLC: silica gel: CH$_2$Cl$_2$–CH$_3$OH: 90–10

Example 2: (n-propyloxy-4 phenoxy)-3 propanediol-1,2 (±)

((Ia); code number 280327)

Dissolve 2 g (0.011 mole) of the product prepared in Example 1 in a mixture of 20 ml CH$_3$CN and 2 ml DMF and then add 1.65 g (0.012 mole) of K$_2$CO$_3$ followed by 4.2 ml (7.4 g; 0.043 mole) of iodopropane.

After 16 h at 80° C., the reaction mixture is concentrated under reduced pressure and then purified directly by flash chromatography (SiO$_2$; eluants CH$_2$Cl$_2$–CH$_3$OH, 95.5–4.5). This yields 1.3 g of a white solid which melts at 95° C. and corresponds to the expected product.

TLC: silica gel: CH$_2$Cl$_2$–CH$_3$OH: 90–10.

Example 3: [(phenylmethyloxy-4) phenoxy]-3 methoxy-1 propanol-2 (±)

((Ib); code number 280077)

To a mixture of 100 g (0.5 mole) of benzyloxy-4 phenol, 98 g (1.75 mole) of finely crushed KOH and 6 g of adogen catalyst, contained in a vessel externally refrigerated to −10° C., add 124 g (1 mole) of chloro-1 methoxy-3 propanol-2 (±), drop by drop over a 1 hour period. Heat at 80° C. for 16 hours, cool, extract with ethyl acetate (3×500 ml), and wash the organic phases together with NaOH 1N (2×500 ml). After drying (MgSO$_4$), filtration and evaporation under reduced pressure, there remains a brown oil which is purified by flash chromatography (SiO$_2$; eluants heptane-ethyl acetate: 65–35). This isolates 75 g of a white solid which melts at 63° C. and corresponds to the expected product.

TLC: silica gel: heptane-ethyl acetate: 50–50.

Example 4: (hydroxy-4 phenoxy)-3 methoxy-1 propanol-2 (±)

((VII); code number 280078)

Weigh into a hydrogenation flask 5.9 g of 10% Pd/C catalyst; after adding 100 ml of ethanol under argon, introduce 59 g (0.20 mole) of the product made as in Example 3, dissolved in 400 ml of ethanol. After stirring for 6 hours under a hydrogen atmosphere, the reaction will be complete. After catalyst filtration and rinsing and evaporation, there remains 36.5 g of a white solid which melts at 90° C. and corresponds to the expected product, for use as described in the following Examples.

Example 5: (n-butoxy-4 phenoxy)-3 methoxy-1 propanol-2 (±)

((Ic); code number 280079)

To a suspension of 10.46 g (0.076 mole) of K$_2$CO$_3$ in 50 ml of DMSO containing 5 g (0.025 mole) of the product made as in Example 4, add 5.4 ml (6.91 g; 0.050 mole) of butyl bromide. Stir the reaction mixture for 16 hours at 60° C. After adding 20 ml of H$_2$O, extract the organic products with ethyl acetate (3×50 ml) and wash with NaOH 1N (5×50 ml). After drying (MgSO$_4$), filtration and evaporation, purify the dark oily product by flash chromatography (SiO$_2$; eluants: heptane-AcOEt: 65–35). The resulting orange oil is then distilled in a Buchi furnace. The distillate corresponds to the expected product and has a boiling point of 150° C. at 0.1 mm Hg pressure.

TLC: silica gel: CH$_2$Cl$_2$–CH$_3$OH: 95–5

Example 6: [(m-chlorophenylmethyloxy-4) phenoxy]-3 phenylmethyloxy-1 propanol-2 (±)

((X); code number 200211)

Into a two-necked flask set up under a refrigerator and in an argon atmosphere, introduce 9 g (0.038 mole) of (chloro-3 benzyloxy-4) phenol, 90 ml of CH$_3$CN, 6.4 g (0.046 mole) of K$_2$CO$_3$ and 9.5 g (0.058 mole) of phenylmethyloxy methyloxirane. After stirring for 16 hours under reflux, separate out the K$_2$CO$_3$ by filtration. Evaporate down the filtrate and take up in ethyl acetate. Wash the organic phase with NaOH 1N (3×50 ml) and dry (MgSO$_4$). Subject the crude product to flash chromatography (SiO$_2$; eluants: heptane-ethyl acetate: 70–30). Recrystallize the white solid product from a mixture of heptane (80) and ethyl acetate (20). This yields 10.4 g of a white solid which melts at 72° C. and corresponds to the expected product.

TLC: silica gel: heptane-ethyl acetate: 70–30.

Example 7: [(chloro-3 phenylmethyloxy)-4 phenoxy]-1 methoxy-2 phenylmethyloxy-3 propane (±)

((XII); code number 200212)

Wash 0.66 g (0.022 mole) of NaH twice in pentane and make a suspension thereof in 10 ml of anhydrous THF. After cooling to 0° C., add drop by drop 8 g (0.020 mole) of the product made as in Example 6, dissolved in 70 ml of THF, followed by 4.3 ml (9.7 g; 0.060 mole) of CH$_3$I. After stirring for 2 hours at room temperature under an argon atmosphere, hydrolyse the reaction mixture by adding 20 ml of iced H$_2$O. Extract the reaction mixture with ethyl acetate (3×80 ml), dry the organic extracts (MgSO$_4$), filter and evaporate down. After flash chromatography (SiO$_2$; eluants: heptane-ethyl acetate: 85–15), this yields 5.6 g of a pale yellow oil corresponding to the expected product.

Example 8: [(chloro-3 phenylmethyloxy)-4 phenoxy]-3 methoxy-2 propanol-1 (±)

((Id); code number 200213)

Into a three-necked hydrogenation flask introduce 0.4 g of 5% Pd/C covered by 20 ml of dioxane. After sweeping with argon then with hydrogen, add 4 g (0.009 mole) of the product obtained in example 7, in solution in 20 ml of dioxane. After stirring for 2 hours at room temperature, filter out and wash the catalyst. On evaporation under reduced pressure, the filtrate is reduced to a rapidly crystallizing oil. The crude product is recrystallized from a mixture of heptane (80) and ethyl acetate (20). The yield is 2.5 g of a white solid which melts at 65° C. and corresponds to the expected product.

TLC: silica gel; heptane-ethyl acetate: 70–30.

Example 9: [(chloro-3 phenylmethyloxy)-4 phenoxy]-1 propanediol-1,2 isopropylidene-1,2 R ((XXVIII); code number 280038)

Into a three-necked flask set up under a refrigerator and in an argon atmosphere, introduce 4.6 g (0.020 mole) of (chloro-3 phenylmethyloxy)-4 phenol, 8.6 g (0.030 mole) of the tosylate of glycerol-2,3 isopropylidene S (+) {$(α)_D^{20}=+4.7°$ (C=4.0; CH$_3$OH)} dissolved in 100 ml of anhydrous DMF and 5.5 g (0.040 mole) of K$_2$CO$_3$. Stir for 16 h at 120° C. and separate off the mineral products by filtration on a Büchner funnel. Evaporate the filtrate down and take up again in ethyl acetate. Wash the organic phase with NaOH 1N (3×20 ml), dry (MgSO$_4$), filter and evaporate down. Purify the residual orange oil by flash chromatography (SiO$_2$; eluants: heptane-ethyl acetate: 80–20). The white solid residue (3 g) corresponds to the expected product.

TLC: silica gel; heptane-ethyl acetate: 60–40.

Example 10: [(chloro-3 phenylmethyloxy)-4 phenoxy]-1 propanediol-2,3 S (+)

((I″a); code number 280039)

Dissolve 2.8 g (0.008 mole) of the product made as in Example 9 in 10 ml of THF. After stirring for 2 h in the presence of 33 ml of HCl 6N, the hydrolysed product will have precipitated out. Filtration and vacuum drying will yield 2.2 g of a white solid corresponding to the expected product $(α)_D^{20}=+4.4°$ (C=1: CH$_2$Cl$_2$)

Melting point: 124° C.

Example 11: [(chloro-3 phenylmethyloxy)-4 phenoxy]-1 methoxy-3 propanol-2 S (+)

((I″c); code number 280040)

Take a solution comprising 0.8 g (0.004 mole) of paratoluene sulphonyl chloride in 2.6 ml (2.56 g; 0.032 mole) of pyridine, cool to 0° C. and add, drop by drop, a solution comprising 1 g (0.003 mole) of the product made as in Example 10 in 2 ml of pyridine. Leave for 16 hours at room temperature. Cool the reaction mixture back to 0° C. and add 4.1 ml of a 4.3N CH$_3$ONa solution (0.018 mole) in CH$_3$OH. Stirring for 16 hours at room temperature leads to a product which is purified after evaporation, by flash chromatography (SiO$_2$; eluants: heptane-ethyl acetate: 60–40). This yields 0.5 g of a white solid corresponding to the expected product.

$(α)_D^{20}=+0.6°$ (C=1; CH$_2$Cl$_2$)

Melting point: 49° C.

Example 12: [(chloro-3 phenylmethyloxy)-4 phenoxy]-1 propanediol-2,3 O.cyclohexylidene S (+)

((XXVI); code number 280041)

Add 5.5 g (0.040 mole) of K$_2$CO$_3$ to a solution comprising 9.8 g (0.030 mole) of the tosylate of glycerol-2,3 O.cyclohexylidene {$(α)_D^{20}=-3.6°$ (C=4; CH$_3$OH)} and 4.6 g (0.020 mole) of (chloro-3 phenylmethyloxy)-4 phenol in 100 ml of anhydrous DMF. After 16 hours stirring, filter off the solids, evaporate the filtrate under reduced pressure, take up again in ethyl acetate (80 ml) and wash the organic phase with NaOH 1N (4×40 ml). Dry (MgSO$_4$), filter and evaporate under reduced pressure. Purify the resulting brown oil by flash chromatography (SiO$_2$; eluants heptane-ethyl acetate: 85–15). This yields 5.2 g of a pale yellow oil corresponding to the expected product.

$(α)_D^{20}=+8.6°$ (C=1; CH$_2$Cl$_2$)

TLC: silica gel; heptane-ethyl acetate: 60–40.

Example 13: [(chloro-3 phenylmethyloxy)-4 phenoxy]-3 propanediol-1,2 R (−)

((I′a); code number 280042)

Add 34 ml of HCl 6N to a solution comprising 3.4 g (0.009 mole) of the product made as in Example 12 in 15 ml of THF. The precipitate formed after stirring for 1 hour at room temperature is a white solid (yield 2 g) which corresponds to the expected product.

$(α)_D^{20}=-4.8°$ (C=1; CH$_3$OH)

Melting point: 124° C.

TLC: silica gel; heptane-ethyl acetate: 50–50.

Example 14: [(chloro-3 phenylmethyloxy)-4 phenoxy]-1 methoxy-3 propanol-2 R (−)

((I′c); code number 280043)

Take a solution comprising 0.96 g (0.050 mole) of recrystallized tosyl chloride in 3.1 ml (3.08 g; 0.039 mole) of pyridine, cool to 0° C. in an external ice bath and add a solution comprising 1.2 g (0.039 mole) of the propanediol-1,2 R (−) made as in Example 13 in 3 ml of pyridine. After stirring for 16 hours at room temperature under an argon atmosphere, add 4.9 ml of CH$_3$ONa 4N solution in methanol, at 0° C. Leave for 16 hours at room temperature, concentrate the reaction mass down under reduced pressure. Flash chromatography (SiO$_2$; eluants heptane-ethyl acetate: 50–50) will yield 0.6 g of the expected product.

$(α)_D^{20}=-1°$ (C=1; CH$_2$Cl$_2$)

Melting point: 51° C.

TLC: silica gel; heptane-ethyl acetate: 30–70.

Example 15: [(chloro-3 phenylmethyloxy)-4]benzaldehyde ((XIV); code number 280118)

To a 1-liter three-necked flask add 50 g (0.41 mole) of 4-hydroxybenzaldehyde, 57 ml (72.4 g; 0.45 mole) of (chloro-3 phenyl)-1 chloromethane, 67.7 g (0.49 mole) of K$_2$CO$_3$, 400 ml of CH$_3$CN, 40 ml of DMF and 6 g (0.04 mole) of KI. After refluxing for 1 hour with vigorous stirring, filter off the mineral products. Concentrate the filtrate down under reduced pressure and take up again in 1.5 liters of water. Filter the precipitate out, wash with water and recrystallize from 200 ml of ethanol. The filtered product, washed with pentane, consists of 90 g of a pale yellow solid (melting below 60° C.), which corresponds to the expected product.

TLC: silica gel; heptane-ethyl acetate: 70–30.

Example 16: [(chloro-3 phenylmethyloxy)-4 phenyl]-1 methoxy-4 butanol-1 (±) ((If); code number 280190) and butanone-1 (±)

((Ig); code number 280189)

Prepare a Grignard solution by dissolving 9.5 g (0.039 mole) of Mg in 8.5 g (0.042 mole) of iodo-1 methoxy-3 propane. Drop by drop, add a solution comprising 9.3 g (0.039 mole) of the product made as in Example 15 in 50 ml of anhydrous ether. Keep the reaction medium under reflux for 30 minutes and then hydrolyse with 100 ml of aqueous NH₄Cl 1N solution. After decantation, dry the organic phase (MgSO₄), filter and evaporate down. Flash chromatographic purification (eluants: heptane-ethyl acetate: 60–40) will isolate two pure solid products:

the less polar product (yield 1 g) is the expected butanone-1 (melting below 60° C.); TLC: silica gel; heptane-ethyl acetate: 50–50;

the more polar product is the expected butanol-1 (yield 6 g; melting below 60° C.);

TLC: silica gel; heptane-ethyl acetate: 50–50.

Example 17: (hydroxy-4 phenyl)-1 methoxy-4 butane ((XVI); code number 280191)

Into a hydrogenation flask place 3 g (0.01 mole) of the butanol-1 (If) made as in example 16, dissolved in 30 ml of 6N hydrochloric ethanol, with 0.6 g of 10% Pd/C catalyst (moisture content 50%). The reaction is complete after stirring for 4 hours at room temperature under a hydrogen atmosphere. Separate the catalyst by filtration. Dry, wash with ethanol and evaporate down under reduced pressure. This yields 1.7 g of a limpid oil corresponding to the expected product.

TLC: silica gel; heptane-ethyl acetate: 40–60.

Example 18: [(cyano-3 phenylmethyloxy-4) phenyl]-1 methoxy-4 butane ((Ih); code number 280192)

Prepare a mixture containing 2.1 g (0.01 mole) of (cyano-3 phenyl)-1 bromomethane, 1.7 g (0.01 mole) of the product made as in Example 17 and 3.9 g (0.028 mole) of K₂CO₃, heat to 50° C. and stir for 1 hour to complete the alkylation reaction; remove the minerals by filtration, concentrate the organic phase down and add 100 ml of water. After extraction with isopropyl ether, decantation, drying (Na₂SO₄), filtration and evaporation under reduced pressure, distill the resulting oil in a Büchi furnace (Eb=210°–220° C./1 mm Hg). (Product yield 1.8 g).

TLC: silica gel-CH₂Cl₂.

EXAMPLE 19: [(chloro-3 phenylmethyloxy)-4]phenol ((XX); code number 200208)

Prepare a suspension of 90.4 g (0.65 mole) of K₂CO₃ and 7 g of KI in 700 ml of CH₃CN containing 72 g (0.65 mole) of p-hydroquinone; drop by drop, add 82.9 ml (105.3 g; 0.65 mole) of metachlorophenylbromomethane. Stir for 2 hours under reflux, remove the minerals by filtration, dry the filtrate and evaporate down under reduced pressure. Take the solid residue up in 500 ml of ethyl acetate. Wash the organic phase with NaOH 1N (3×200 ml), dry (MgSO₄), filter and evaporate down. Purify the crude product by flash chromatography (SiO₂; eluants: CH₂Cl₂–CH₃OH: 98–2). This yields 53.3 g of an orange solid which melts at 119° C. and corresponds to the expected product.

TLC: silica gel: heptane-ethyl acetate: 70–30.

EXAMPLE 20: [(chloro-3 phenylmethyloxy)-4 phenyloxy]-3 propanol-1

((Ij); code number 200215)

Prepare a solution of 6.37 g (0.046 mole) of K₂CO₃ in 90 ml of CH₃CN containing 9 g (0.038 mole) of the product with code number 200208, and drop by drop add 3.57 ml (4 g; 0.042 mole) of chloro-3 propanol-1. After stirring for 20 hours under reflux, separate the minerals by filtration and dry. Evaporate the filtrate down and take up in 100 ml of ethyl acetate. Wash the organic phase with NaOH 1N (3×50 ml), dry (MgSO₄), filter and evaporate down under reduced pressure. Purify the crude product by flash chromatography (SiO₂; eluants: heptane-ethyl acetate: 50–50). This yields 6 g of a pale yellow solid which melts at 106° C. and corresponds to the expected product.

TLC: silica gel; heptane-ethyl acetate: 70–30.

EXAMPLE 21: [(chloro-3 phenylmethyloxy)-4 phenoxy]-3 methoxy-1 propane ((Ik); code number 200216)

Wash 0.18 g (0.006 mole) of 80% NaH twice with pentane, cover with 5 ml of anhydrous THF, and add drop by drop, keeping the temperature at 0° C., 10 ml of anhydrous THF solution containing 1.5 g (0.005 mole) of the product made as in Example 20. After 5 minutes, add 1.1 ml of CH₃I (2.5 g; 0.015 mole). The reaction is completed after stirring for 4 hours at room temperature. Add 5 ml of water and then extract with ethyl acetate (3×20 ml). The usual treatment is followed by flash chromatography (SiO₂; eluants heptane-ethyl acetate: 85–15). This yields 1.5 g of a white solid (melting below 50° C.) which corresponds to the expected product.

TLC: silica gel; heptane-ethyl acetate: 70–30.

EXAMPLE 22: [(chloro-3 phenylmethyloxy)-4 phenyloxy]-3 mesyloxy-1 propane ((XXII); code number 200217)

To 20 ml of CH₂Cl₂, add first 2 g (0.007 mole) of the product made as in Example 20, then 0.64 ml (0.94 g; 0.008 mole) of mesyl chloride, and finally, with the temperature below −5° C., 1.14 ml (0.83 g; 0.008 mole) of NEt₃. To complete the reaction, stir for 3 hours and allow the temperature to recover. Wash the reaction mass (2×10 ml H₂O), dry the organic phase (MgSO₄), filter and evaporate down under reduced pressure. Thus yield 2.4 g of an oil which crystallizes from ether to form a cream solid (1.9 g) which melts at a temperature below 50° C. and corresponds to the expected product.

EXAMPLE 23: [(chloro-3 phenylmethyloxy)-4 phenyloxy]-3 cyano-1 propane ((Il); code number 200218)

Add to 5 ml of DMSO at 0° C. 0.5 g (0.001 mole) of the mesylate made as in Example 2 and 0.2 g (0.004 mole) of NaCN. After stirring for 24 hours at room temperature, dilute the reaction mass with 2 ml of water (which produces heating and precipitation). Extract with 3×5 ml of ethyl acetate, dry (MgSO₄), filter and evaporate down. Recrystallize the resulting pale yellow solid (0.35 g) from a mixture of heptane (80) and ethyl acetate (20). This yields 0.3 g of a white solid (melting point 71° C.) which corresponds to the expected product.

TLC: silica gel; heptane-ethyl acetate: 50–50.

EXAMPLE 24: [(chloro-3 phenylmethyloxy)-4 phenyloxy]-3 N-methylamino-1 propane ((Im); code number 200219)

Mix together in a vessel 0.8 g (0.002 mole) of the mesylate made as in Example 22, dissolved in 8 ml of a 50/50 mixture of EtOH and CH₂Cl₂, and 0.87 ml (0.67 g; 0.022 mole) of N-methylamine (both reagents cooled). Close the vessel tightly and stir for 16 hours. After partial evaporation, take up the reaction mixture with 30 ml of ethyl acetate and 10 ml of water, and treat with NaOH 1N (3×10 ml).

Dry the organic phase (MgSO₄), filter and evaporate down under reduced pressure. This yields an orange oil corresponding to the expected product, which crystallizes slowly. Treatment with 1.4 ml of 2N hydrochloric ethanol, in the presence of ether, yields 0.6 g of the corresponding hydrochloride (melting point 173° C.).

TLC: silica gel; CH₂Cl₂-CH₃OH: 95.5.

The following Tables I to III list the chemical properties of a certain number of the compounds covered by the invention. The abbreviations "Cal" and "Tr" in the column headed "Elemental Analysis" stand for "calculated" and "found", respectively.

TABLE I

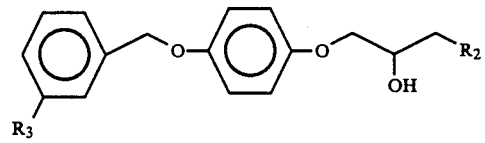

(I)

| Code Number | $R_3$ | $R_2$ | Absolute Configuration | General Formula | Molecular Weight | ELEMENTAL ANALYSIS | | | | Melting Point (°C.) | $[\alpha]_D^{20}$ |
|---|---|---|---|---|---|---|---|---|---|---|---|
| | | | | | | | % C | H | N | | |
| 340482 | F | OH | (±) | $C_{16}H_{17}FO_4$ | 292.296 | Cal. | 65.74 | 5.86 | — | 114 | |
| | | | | | | Tr. | 65.88 | 5.97 | — | | |
| 340494 | Cl | OH | (±) | $C_{16}H_{17}ClO_4$ | 308.753 | Cal. | 62.24 | 5.55 | — | 120 | |
| | | | | | | Tr. | 62.00 | 5.68 | — | | |
| 340495 | I | OH | (±) | $C_{16}H_{17}IO_4$ | 400.200 | Cal. | 48.02 | 4.28 | — | 135 | |
| | | | | | | Tr. | 47.98 | 4.30 | — | | |
| 280331 | Br | OH | (±) | $C_{16}H_{17}BrO_4$ | 353.206 | Cal. | 54.40 | 4.85 | — | 126 | |
| | | | | | | Tr. | 54.00 | 4.89 | — | | |
| 280329 | CF₃ | OH | (±) | $C_{17}H_{17}F_3O_4$ | 342.306 | Cal. | 59.65 | 5.01 | — | 78 | |
| | | | | | | Tr. | 59.36 | 4.92 | — | | |
| 280328 | CH₃O | OH | (±) | $C_{17}H_{20}O_5$ | 304.331 | Cal. | 67.09 | 6.62 | — | 74 | |
| | | | | | | Tr. | 67.04 | 6.50 | — | | |
| 280330 | NO₂ | OH | (±) | $C_{16}H_{17}NO_6$ | 319.304 | Cal. | 60.18 | 5.37 | 4.39 | 61 | |
| | | | | | | Tr. | 60.09 | 5.30 | 4.31 | | |
| 280415 | CN | OH | (±) | $C_{17}H_{17}NO_4$ | 299.314 | Cal. | 68.21 | 5.73 | 4.68 | 87 | |
| | | | | | | Tr. | 67.66 | 5.88 | 4.48 | | |
| 280039 | Cl | OH | S(+) | $C_{16}H_{17}ClO_4$ | 308.753 | Cal. | — | — | — | 124 | +4.4°* |
| | | | | | | Tr. | — | — | — | | |
| 280042 | Cl | OH | R(−) | $C_{16}H_{17}ClO_4$ | 308.753 | Cal. | — | — | — | 124 | −4.8°** |
| | | | | | | Tr. | — | — | — | | |
| 200209 | Cl | OCH₃ | (±) | $C_{17}H_{19}ClO_4$ | 322.779 | Cal. | 63.25 | 5.93 | — | 50 | |
| | | | | | | Tr. | 63.47 | 6.15 | — | | |
| 280040 | Cl | OCH₃ | S(+) | $C_{17}H_{19}ClO_4$ | 322.779 | Cal. | 63.25 | 5.93 | — | 49 | +0.6°* |
| | | | | | | Tr. | 63.51 | 6.06 | — | | |
| 280043 | Cl | OCH₃ | R(−) | $C_{17}H_{19}ClO_4$ | 322.779 | Cal. | 63.25 | 5.93 | — | 51 | −1°* |
| | | | | | | Tr. | 63.45 | 5.71 | — | | |
| 280417 | Br | OCH₃ | (±) | $C_{17}H_{19}BrO_4$ | 367.231 | Cal. | 55.60 | 5.22 | — | 64 | |
| | | | | | | Tr. | 55.35 | 5.38 | — | | |
| 280418 | I | OCH₃ | (±) | $C_{17}H_{19}IO_4$ | 414.226 | Cal. | 49.29 | 4.62 | — | 75 | |
| | | | | | | Tr. | 49.59 | 4.63 | — | | |
| 280416 | CN | OCH₃ | (±) | $C_{18}H_{19}NO_4$ | 313.340 | Cal. | 68.99 | 6.11 | 4.47 | <60 | |
| | | | | | | Tr. | 68.04 | 6.04 | 4.52 | | |
| 280077 | H | OCH₃ | (±) | $C_{17}H_{20}O_4$ | 313.340 | Cal. | — | — | — | 63 | |
| | | | | | | Tr. | — | — | — | | |

*(C = 1; CH₂Cl₂)
**(C = 1; CH₃OH)

TABLE II

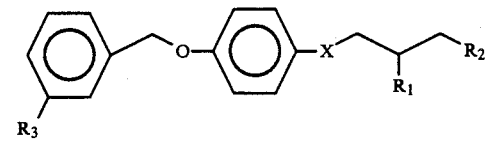

(I)

| Code Number | $R_3$ | X | $R_1$ | $R_2$ | Absolute Configuration | General Formula | Molecular Weight | ELEMENTAL ANALYSIS | | | | Melting Point (°C.) |
|---|---|---|---|---|---|---|---|---|---|---|---|---|
| | | | | | | | | | % C | H | N | |
| 200123 | Cl | CH₂ | H | OH | — | $C_{17}H_{19}ClO_2$ | 290.799 | Cal. | 70.21 | 6.59 | — | 52 |
| | | | | | | | | Tr. | 69.57 | 6.76 | — | |
| 200124 | Cl | CH₂ | H | OCH₃ | — | $C_{18}H_{21}ClO_2$ | 304.805 | Cal. | 70.92 | 6.94 | — | Oil |
| | | | | | | | | Tr. | 71.13 | 7.13 | — | |
| 200215 | Cl | O | H | OH | — | $C_{16}H_{17}ClO_3$ | 292.753 | Cal. | 65.64 | 5.85 | — | 106 |
| | | | | | | | | Tr. | 65.65 | 5.77 | — | |
| 200216 | Cl | O | H | OCH₃ | — | $C_{17}H_{19}ClO_3$ | 306.779 | Cal. | 66.55 | 6.24 | — | >50 |
| | | | | | | | | Tr. | 66.26 | 6.34 | — | |

TABLE II-continued

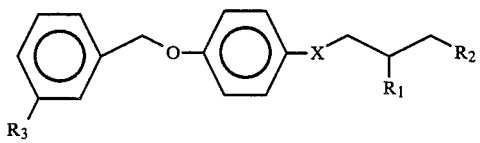

(I)

| Code Number | R3 | X | R1 | R2 | Absolute Configuration | General Formula | Molecular Weight | ELEMENTAL ANALYSIS | % | C | H | N | Melting Point (°C.) |
| --- | --- | --- | --- | --- | --- | --- | --- | --- | --- | --- | --- | --- | --- |
| 200219 | Cl | O | H | NHCH3 | — | $C_{17}H_{20}ClNO_2$, HCl | 342.260 | | Cal. Tr. | 59.65 59.49 | 6.18 6.23 | 4.09 4.23 | 173 |
| 200218 | Cl | O | H | CN | — | $C_{17}H_{16}ClNO_2$ | 301.763 | | Cal. Tr. | 67.66 67.62 | 5.34 5.39 | 4.64 4.70 | 71 |
| 200213 | Cl | O | OCH3 | OH | (±) | $C_{17}H_{19}ClO_4$ | 322.779 | | Cal. Tr. | 63.25 63.27 | 5.93 5.93 | — — | 65 |
| 200210 | Cl | O | OCH3 | OCH3 | (±) | $C_{18}H_{21}ClO_4$ | 336.805 | | Cal. Tr. | 64.19 63.99 | 6.28 6.53 | — — | Oil |
| 280189 | Cl | CO | H | OCH3 | — | $C_{18}H_{19}ClO_3$ | 318.789 | | Cal. Tr. | 67.81 67.76 | 6.01 6.13 | — — | <60 |
| 280190 | Cl | CHOH | H | OCH3 | (±) | $C_{18}H_{21}ClO_3$ | 320.805 | | Cal. Tr. | 67.39 67.28 | 6.60 6.68 | — — | <60 |
| 280192 | CN | CH2 | H | OCH3 | — | $C_{19}H_{21}NO_2$ | 295.366 | | Cal. Tr. | 77.26 76.64 | 7.17 7.22 | 4.74 4.29 | * |

*: Eb = 210–220° C./1 mmHg

TABLE III

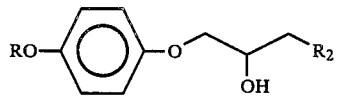

(I)

| Code Number | RO | R2 | Absolute Configuration | General Formula | Molecular Weight | ELEMENTAL ANALYSIS | % | C | H | N | Melting Point (°C.) |
| --- | --- | --- | --- | --- | --- | --- | --- | --- | --- | --- | --- |
| 280079 | $C_4H_9O$ | OCH3 | (±) | $C_{14}H_{22}O_4$ | 254.316 | | Cal. Tr. | 66.11 65.82 | 8.72 8.99 | — — | Oil |
| 280080 | $C_5H_{11}O$ | OCH3 | (±) | $C_{15}H_{24}O_4$ | 268.342 | | Cal. Tr. | 67.13 67.20 | 9.02 9.15 | — — | Oil |

The compounds (Io) specified above have been studied on laboratory animals and exhibited an inhibitive action on monoamine oxydases in general and type B monoamine oxydase in particular.

Their activity was demonstrated by a test which allows the in vitro measurement of inhibitive action on the two forms A and B of monoamine oxydase in rat brain tissue; the procedure is described in J. Pharm. Pharmacol., 1983, 35, 161–165.

The results obtained with a number of the compounds (Io) are presented in the following Table IV.

TABLE IV

Inhibition constants $K_{IA}$ and $K_{IB}$ on forms A and B of monoamine oxydase (homogenized entire brain of a male rate (Sprague-Dawley): 1 g of tissue to 16 ml of phosphate buffer at pH = 7.4).

| Code number of compound tested | IN VITRO INHIBITION OF MONOAMINE DEOXYDASE | | | | | |
| --- | --- | --- | --- | --- | --- | --- |
| | no pre-incubation | | | after 20 min pre-incubation | | |
| | $K_{IA}$ | $K_{IB}$ | $K_{IA}/K_{IB}$ | $K_{IA}$ | $K_{IB}$ | $K_{IA}/K_{IB}$ |
| 280040 | — | — | — | 1648 | 9 | 183 |
| 200123 | >1724 | 232 | >7 | — | — | — |
| 200213 | >5172 | 543 | >9.5 | — | — | — |
| 200210 | >1724 | 403 | >4 | >1724 | 570 | >3 |
| 280190 | — | — | — | 5431 | 79 | 69 |

The inhibition constants were calculated from the formula: $K_I = CI_{50}/1 + [S]/K_m$ taking [S] = 48 μM for ($^{14}$C) serotonine and $K_m$ = 100 μM, or [S] = 12 μM for ($^{14}$C) phenylethylamine and $K_m$ = 6 μM as the selective substrates for forms A and B respectively of monoamine oxydase.

Furthermore, no signs of toxicity were observed over a 24 hour period from oral administering compounds (Io) to rodents at doses of 1000 mg per kg of body weight.

Thus, the compounds (Io) can be used to prepare drugs for the inhibition of monoamine oxydases in general and the selective inhibition of type B monoamine oxydase in particular, which drugs can be used therapeutically, notably for treating neurological disorders related to pathological ageing, memory problems, changes in temperament, schizophrenia, psychaesthenia or psychic retardation associated with ageing, certain forms of depression and Parkinson's disease.

These drugs can be administered to human patients or any hot-blooded animals, under various pharmaceutical forms well known in the art, and notably in the form of preparations formulated with a view to oral, parenteral or rectal administration.

For oral administration, the said preparations can be presented in the form of tablets, pills or capsules prepared by the known techniques using known carriers and excipients such as binders, inert fillers, lubricants and disintegration agents; they can also be administered in the form of solutions, syrups or suspensions.

For parenteral administration, the preparations of the invention can be presented in the form of injectable solutions, suspensions or emulsions containing a parenteral acceptable liquid vehicle, oily or aqueous.

For rectal administration, the compounds can be presented in the form of suppositories containing the bases usually employed for suppositories.

The dosage at which the active principles, i.e., the compounds (Io), can be administered will depend particularly on the method of administration, the body weight of the patient and the therapeutic activity of the compound in question. In general, orally administered dosages can be up to 200 mg of the active principle per day (in one or more portions); for parenteral administration, up to 300 mg of the active principle can be administered daily (in one or two daily injections); for rectal administration, up to 300 mg of the active principle can be administered daily (in one or two suppositories per day).

We claim:

1. A compound of the formula

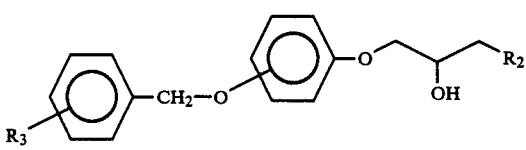

wherein:
$R_2$ is a —$C_1$-$C_4$-alkoxy group; and $R_3$ is —H, -halogen, —$C_1$-$C_4$alkyl, —$C_1$-$C_4$ alkoxy, —$CF_3$, —$NO_2$ or —C≡N.

2. A compound of the formula

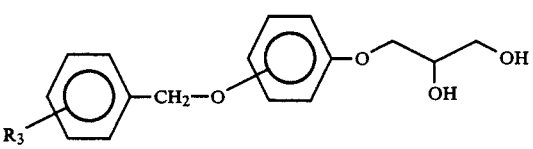

wherein:
$R_3$ is -halogen, —$C_1$-$C_4$ alkoxy, —$CF_3$, —$NO_2$ or —C≡N.

3. A compound of the formula

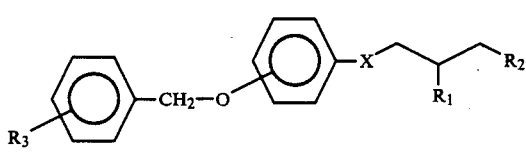

wherein:
$R_2$ is a —$C_1$-$C_4$ alkoxy group, X is —O— and $R_1$ is —$C_1$-$C_4$ alkoxy, X is —CH(—OH)— and $R_1$ is —H or X is —CH$_2$— and $R_1$ is —H;
or $R_2$ is an —OH group, X is —O— and $R_1$ is —$C_1$-$C_4$ alkoxy, or X is —CH$_2$— and $R_1$ is —H;
and $R_3$ is —H, -halogen, —$C_1$-$C_4$ alkyl, —$C_1$-$C_4$ alkoxy, —$CF_3$, —$NO_2$ or —C≡N.

4. A compound of the formula

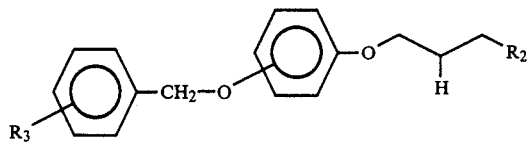

wherein:
$R_2$ is —$C_1$-$C_4$ alkoxy or —OH; and
$R_3$ is m-halo, —$C_1$-$C_4$ alkyl, —$C_1$-$C_4$ alkoxy, —$CF_3$, —$NO_2$ or —C≡N.

5. A compound according to claim 1, wherein the

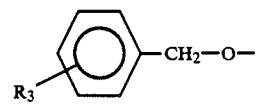

group is in the para position.

6. A compound according to claim 2, wherein the

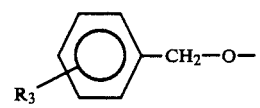

group is in the para position.

7. A compound according to claim 3, wherein the

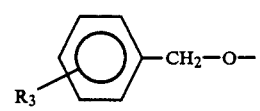

group is in the para position.

8. A compound according to claim 4, wherein the

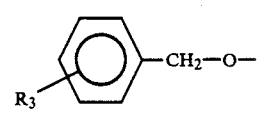

group is in the para position.

9. A compound according to claim 1, wherein $R_3$ is in the meta position.

10. A compound according to claim 2, wherein $R_3$ is in the meta position.

11. A compound according to claim 3, wherein $R_3$ is in the meta position.

12. A compound according to claim 4, wherein $R_3$ is a meta-halo group or $R_3$ is in the meta position and is —$C_1$-$C_4$ alkyl, —$C_1$-$C_4$ alkoxy, —$CF_3$, —$NO_2$ or —C≡N.

13. A compound according to claim 5, wherein $R_3$ is in the meta position.

14. A compound according to claim 6, wherein $R_3$ is in the meta position.

15. A compound according to claim 7, wherein $R_3$ is in the meta position.

16. A compound according to claim 8, wherein $R_3$ is a meta-halo group or $R_3$ is in the meta position and is —$C_1$-$C_4$ alkyl, —$C_1$-$C_4$ alkoxy, —$CF_3$, —$NO_2$ or —C≡N.

17. A compound according to claim 1, wherein $R_2$ is an —$OCH_3$ group.

18. A compound according to claim 4, wherein $R_2$ is an —$OCH_3$ group.

19. A compound according to claim 3, wherein one or both of $R_1$ and $R_2$ are each independently an —$OCH_3$ group.

20. A pharmaceutical or veterinary composition comprising a monoamine oxidase inhibiting amount of a compound according to claim 1 and a pharmaceutically or a veterinarian acceptable carrier.

21. A pharmaceutical or veterinary composition comprising a monoamine oxidase inhibiting amount of a compound according to claim 2 and a pharmaceutically or a veterinarian acceptable carrier.

22. A pharmaceutical or veterinary composition comprising a monoamine oxidase inhibiting amount of a compound according to claim 3 and a pharmaceutically or a veterinarian acceptable carrier.

23. A pharmaceutical or veterinary composition comprising a monoamine oxidase inhibiting amount of a compound according to claim 4 and a pharmaceutically or a veterinarian acceptable carrier.

24. A method of inhibiting monoamine oxidase in a patient which comprises administering to said patient an effective amount of a compound according to claim 1.

25. A method of inhibiting monoamine oxidase in a patient which comprises administering to said patient an effective amount of a compound according to claim 2.

26. A method of inhibiting monoamine oxidase in a patient which comprises administering to said patient an effective amount of a compound according to claim 3.

27. A method of inhibiting monoamine oxidase in a patient which comprises administering to said patient an effective amount of a compound according to claim 4.

* * * * *